United States Patent [19]

Menton et al.

[11] Patent Number: 6,159,703
[45] Date of Patent: Dec. 12, 2000

[54] ASSAYS

[75] Inventors: Jeanette E. Menton, Bedford; Paul R. Sheard, Wilby, both of United Kingdom

[73] Assignee: Unipath Limited, Basingstoke, United Kingdom

[21] Appl. No.: 08/713,849

[22] Filed: Sep. 13, 1996

[30] Foreign Application Priority Data

Sep. 14, 1995 [EP] European Pat. Off. ............. 95306506

[51] Int. Cl.⁷ ................. G01N 33/571; G01N 33/00; G01N 1/00; C12N 9/99
[52] U.S. Cl. ................. 435/7.36; 435/184; 435/962; 436/94; 436/174; 436/175
[58] Field of Search ................. 435/7.36, 962, 435/184; 436/94, 174, 175

[56] References Cited

U.S. PATENT DOCUMENTS

| | | | |
|---|---|---|---|
| 4,760,131 | 7/1988 | Sundsmo et al. | 530/356 |
| 4,914,041 | 4/1990 | Thrasher . | |
| 4,916,057 | 4/1990 | Thompson et al. . | |
| 5,302,405 | 4/1994 | Hsieh et al. . | |
| 5,387,511 | 2/1995 | Davidson et al. . | |
| 5,389,547 | 2/1995 | Tanaka et al. | 436/94 |
| 5,571,895 | 11/1996 | Kurokawa et al. | 530/399 |

FOREIGN PATENT DOCUMENTS

| | | |
|---|---|---|
| WO 89/07765 | 8/1989 | WIPO . |
| WO 89/08262 | 9/1989 | WIPO . |
| WO 90/02336 | 3/1990 | WIPO . |
| WO 94/05166 | 3/1994 | WIPO . |

OTHER PUBLICATIONS

Akhlaq A. Farooqui, "Purification of Enzymes by Heparin–Sepharose Affinity Chromatography", Journal of Chromatography, Chromatographic Reviews, 184 (1980), pp. 335–345.

Shaul G. Massry, M.D., et al., Chapter 95:" Urinalyis", Textbook of Nephrology, vol. 2, 3rd Edition, 1995, pp. 1753, 1775, and 1765.

John Bernard Henry, M.D., "Medical Microscopy and Examination of Other Body Fluids", Todd Sanford Davidson Clinical Diagnosis and Management by Laboratory Methods, 16th Ed., vol. 1., pp. 625–626.

Hammerschlag et al, "Comparison of two enzyme immunoassays to culture for the diagnosis of chlamydial conjunctivitis and respiratory infections infants.", Journal of Clinical Microbiology, vol. 28, No. 8, pp. 1725–1727, Aug. 1, 1990.

Moulder, "Order II. Chlamydiales", Bergey's Manual of Systematic Bacteriology, vol. 1, pp. 729–239, Jan. 1, 1984.

*Primary Examiner*—Rodney P. Swartz
*Attorney, Agent, or Firm*—Pillsbury Madison & Sutro LLP

[57] ABSTRACT

Enhanced extraction and assay of solubilized lipopolysaccharide antigens from bacteria such as Chlamydia by the use of a buffer containing an anionic polysaccharide, especially heparin, and surface active agent, especially CHAPS or CHAPSO.

7 Claims, No Drawings

ASSAYS

FIELD OF THE INVENTION

This invention relates to assays, and in particular to methods for preparing aqueous samples for use in assays for lipopolysaccharide antigens.

BACKGROUND TO THE INVENTION

Lipopolysaccharide antigens are important indicators of the presence of certain pathogenic bacteria, notably Chlamydia. Such assays require the preparation of an aqueous extract from a clinical sample suspected of containing the organisms. The sample may, for example, be in the form of a clinical swab taken from a patient. An extraction buffer is used to free lipopolysaccharide antigen from organisms that may be present in the sample. A typical extraction buffer will contain lysing agents such as detergents. The extraction procedure may involve heating of the sample in the extraction buffer, for example to a temperature in the range of 80° to 100° C. After several minutes a sufficient quantity of lipopolysaccharide antigen will have been released from any organisms present to provide basis for an accurate assay.

It is already well known that clinical samples often contain irrelevant components which may interfere with the sensitivity of a lipopolysaccharide antigen assay. Cations are a particular nuisance. EP-A-392865 discusses this problem and recommends that divalent cations should be removed from the system, for example, by chelation with agents such as EDTA. EP-A-392865 is particularly concerned with the unwanted presence of divalent cations such as zinc and magnesium. Other cationically-charged materials may also be present in the clinical sample. Any of these cationic materials may interfere with the sensitivity of a lipopolysaccharide antigen assay. We believe that this interference arises because the cations bind to a negatively charged region of the lipopolysaccharide molecule and block an important binding site against which antibodies useful in such an assay are raised.

GENERAL DESCRIPTION OF THE INVENTION

By the invention we have found that a substantial reduction in interference caused by cations during a lipopolysaccharide antigen assay can be brought about by using an anionic polysaccharide.

The invention provides an assay for lipopolysaccharide antigen, conducted in the presence of an anionic polysaccharide in an amount sufficient to reduce interference caused by cations.

Preferably the anionic polysaccharide is a glycosaminoglycan, such as heparin. Alternatives include heparin sulphate and dermatan sulphate.

The invention is particularly applicable when the lipopolysaccharide antigen is bacterial, e.g. when the bacteria are Chlamydia.

The invention also provides an aqueous extraction buffer for solubilizing antigenic material in bacteria and the like, containing an anionic polysaccharide in an amount sufficient to enhance assay sensitivity.

An important embodiment of the invention is an aqueous extraction buffer for use in solubilizing lipopolysaccharide antigen in Chlamydia, containing a glycosoaminoglycan, especially heparin, in an amount sufficient to enhance assay sensitivity. Preferably the buffer contains at least about 0.1 mg/ml heparin. Normally it does not need to contain more than about 10 mg/ml heparin.

Another embodiment of the invention is a method of preparing an aqueous assay sample from clinical material suspected of containing micro-organisms, such as Chlamydia, which express lipopolysaccharide antigen, wherein the clinical material or an aqueous extract thereof is contacted with an anionic polysaccharide, especially a glycosoaminoglycan such as heparin, in insolubilized form.

In one embodiment, the invention provides a procedure for extracting solubilized antigenic material from cellular biological material, such as bacteria, wherein the cellular material is treated with an aqueous solution of a surface active agent, in the presence of an anionic polysaccharide. Preferably the surface active agent is zwitterionic. More preferably, the surface active agent is 3-(3-chlolamidopropyl)dimethylammonio-1-propanesulfonate (conveniently known as CHAPS) or 3-(3-chlolamidopropyl) dimethylammonio-2-hydroxyl-1-propanesulfonate (conveniently known as CHAPSO), or mixtures thereof.

An especially effective extraction of lipopolysaccharide antigen from Chlamydia species such as *Chlamydia trachomitis, C.psittaci* and *C.twar*, is achieved if the extraction is performed using an aqueous solution of heparin and a zwitterionic surface active agent, especially CHAPS and/or CHAPSO.

Preferably, the extraction is conducted at elevated temperature, for example in excess of about 50° C., for a period of time sufficient to solubilize the antigenic material. More preferably, the extraction temperature is at least about 60° C. In general, the extraction temperature need not be greater than about 100° C., and is preferably not greater than about 90° C. Ideally, the extraction temperature is about 80° C. The stage of the extraction conducted at such elevated temperature should generally last for at least about 5 minutes.

Preferably, the quantity of surface active agent in the aqueous extraction medium is at least about 0.1% by weight. Preferably the quantity of surface active agent is not greater than about 2%, and more preferably not greater than about 1% by weight.

The pH of the extraction medium should generally be in the range of about 7.5 to about 9.

The heparin or other anionic polysaccharides can be used either in soluble or insoluble form as desired. Heparin is available commercially in either form. One option is to have the anionic polysaccharide as a soluble component in the extraction buffer or added as a soluble component at a later stage before commencement of the actual assay procedure. Presence as a component in an extraction buffer is probably the most convenient from the user's point of view. Alternatively, an aqueous sample/extract can be contacted with an insolubilized form of the anionic polysaccharide, for example, heparin bound to a solid surface such as resin beads. The insolubilized anionic polysaccharide can be removed from the aqueous composition before the actual assay is conducted. For example beads can be centrifuged or filtered out. A solid phase of greater bulk, for example a high surface area dipstick on which the heparin is bound can be separated from the aqueous composition by manual extraction or decantation of the liquid. A variety of alternative formats will suggest themselves readily to the skilled reader. The essential objective is that the aqueous composition containing the lipopolysaccharide antigens to be assayed is exposed to the anionic polysaccharide under circumstances which permit the anionic polysaccharide to bind with and in effect, remove from the system at least a proportion of any cationic components present which might interfere with the accuracy of the lipopolysaccharide antigen assay. For any given assay procedure and format the optimum amount and presentation of the anionic polysaccharide can be determined by simple experiment.

In a typical extraction procedure according to the invention, a biological sample obtained from a patient suspected of carrying a Chlamydia infection, for example, is contacted with the extraction medium. Appropriate samples can take the form, for example, of genital, rectal or ocular swabs, or centrifugal pellets from liquids such as early morning urine. Extraction, for example at 80° C. for 10 minutes, is followed by a brief period, for example 5 minutes, during which the extraction medium is allowed to cool. Thereafter the extraction medium can be separated from solid matter, for example by removal of the swab and filtration of the solution to provide a sample liquid containing any extracted antigen ready for use in any suitable assay procedure. The subsequent assay can involve any conventional assay technique, such as radioimmunoassay or enzyme-linked immunoassay. The extracted sample is ideal for use in an immunochromatographic assay procedure such as described and claimed in EP-A-291194, especially using a nitrocellulose solid phase and an antibody reagent labelled with a direct particulate label such as coloured latex particles. The use of heparin together with CHAPS and/or CHAPSO enhances the sensitivity of a Chlamydia assay which involves anti-lipopolysaccharide antigen antibodies as specific binding reagents.

EXAMPLES

Example 1

An extraction procedure for *Chlamydia trachomatis* can be performed as follows. This provides an extract suitable for use in an immunoassay.

The extraction procedure utilises:

a) Disposable, flexible plastic "test tubes" each capable of holding a volume (eg. 5 ml) of liquid and of accommodating the end of a conventional sampling swab.

b) A heating block in which such tubes can be inserted to permit the contents of the tube to be heated to a temperature in the range 50–100° C. and held at that temperature for at least a number of minutes.

c) Means for filtering the liquid contents of the tube at the end of the extraction procedure. Conveniently this can take the form of a filter plug incorporated in a perforated stopper with which the tube can be closed and through which the liquid contents can be expelled.

d) An extraction buffer having the following formulation:
0.25 M TRIS pH 8.5 containing
    0.85% Sodium chloride
    0.25% CHAPSO
    5 mM EDTA
    1% Bovine serum albumin
    1 mg/ml Heparin (SIGMA)

To conduct the extraction, a pre-determined quantity (for example 600 μl) of extraction buffer is placed in a tube. A genital swab from a patient suspected of carrying a Chlamydia infection is placed in the tube, and the tube and contents are then incubated in the heating block at a temperature of approximately 80° C. for 10 minutes. The tube is removed from the heating block and allowed to cool for 5 minutes. The swab is lifted out of the extraction buffer and, before the swab is removed completely from the tube, the sides of the tube are pressed in gently by hand to squeeze liquid from the swab. The swab can then be removed completely from the tube and discarded. A perforated stopper containing a filter plug is inserted in the top of the tube, and the liquid contents of the tube can be expelled therethrough to provide an essentially clear liquid sample containing any extracted Chlamydia lipopolysaccharide antigen for use in a subsequent assay. If desired, one or more assay reagents, such as labelled antibodies, can be added to the contents of the tube before the filter/stopper is applied to the tube.

The assay can be conducted using any established procedure. Preferably this is accomplished by means of a particle-labelled reagent becoming bound, in a sandwich or competition format assay in the presence of lipopolysaccharide antigen, to reveal the result in a small detection zone, e.g. narrow line, on a porous carrier material such as a nitrocellulose strip, as generally described in EP-A-291194.

Example 2

The following experiments demonstrate the ability of heparin, either in soluble or insolubilized form, to enhance the sensitivity of a Chlamydia lipopolysaccharide antigen assay.

Materials and Conditions

Materials used:

Chlamydia negative female endocervical swabs were washed in saline, washes from five swabs were then pooled. New swab (C) pools were made for each experiment.

Protamine (a small protein molecule) was used to simulate clinical sample interference, at 0.001 mg/ml.

Heparin resin (SIGMA H-5380, Lot No. 61 H 9570) was used as a method for removing clinical interferences. Slurries were made using 50% resin to 50% water. 250 μl of slurry was centrifuged at 13500 rpm for 5 minutes, the supernatant removed and 300 μl sample added. Slurry was then mixed end-over-end for 5 minutes. The mixture was centrifuged at 13500 rpm for 5 minutes. The supernatant was then assayed as detailed below.

Extraction buffer (as in Example 1) with and without 1 mg/ml soluble heparin (SIGMA).

Procedure: Heat sample in a plastics extraction tube, with filter/dropper cap, at 80° C.±2° C. for 10 minutes. Allow to cool to room temperature for 5 minutes. Place filter cap on extraction tube, and squeeze 5 drops from tube onto a commercially-available "CLEARVIEW Chlamydia" (Unipath Ltd, UK) assay device, as broadly described in EP-A-291194. This uses blue-coloured latex (polystyrene) particles carrying anti-lipopolysaccharide antibodies as a mobile reagent, and anti-LPS antibodies immobilized in a test line as a capture reagent, on a nitrocellulose strip. The assay result is revealed as visible line in test window. Line intensity was assessed optically in arbitrary units, as a measure of antigen detection relative to a standardized control sample.

Experiment 1

Demonstrating the removal by heparin resin of cationic interferences from clinical samples.

Resin-treated swab pool and untreated swab pool were added to extraction buffer in the presence of a known amount of Chlamydia antigen.

a) 50 μl swab pool+15 μl antigen+535 μl extraction buffer=3.5 units (62%)

b) 50 μl resin-treated swab pool+15 μl antigen+535 μl extraction buffer=6.0 units (105%)

c) 15 μl antigen+585 μl extraction buffer (control)=5.7 units (100%)

Experiment 2

Demonstrating the ability of soluble heparin to inhibit interferences present in clinical samples.

Swab pool was then added to extraction buffer with and without dissolved heparin, in the presence of a known amount of Chlamydia antigen.

a) 50 µl swab pool+15 µl antigen+535 µl extraction buffer (no heparin)=9.9 units (65%)
b) 50 µl swab pool+15 µl antigen+535 µl extraction buffer with heparin=13.3 units (88%)
c) 15 µl antigen+585 µl extraction buffer (control)=15.1 units (100%)

Experiment 3

Demonstrating the ability of dissolved heparin or heparin resin to inhibit interferences present in clinical samples.

Resin-treated swab pool and untreated swab pool were then added to extraction buffer (no heparin) with a known amount of Chlamydia antigen.

The untreated swab pool was also tested using extraction buffer with dissolved heparin.

a) 25 µl swab pool+15 µl antigen+560 µl extraction buffer=3.54 units (67%)
b) 25 µl swab pool+15 µl antigen+560 µl extraction buffer with heparin=6.14 units (116%)
c) 25 µl of resin-treated swab pool+15 µl antigen+560 µl extraction buffer=6.49 units (122%)
d) 15 µl antigen+585 µl extraction buffer (control)=5.31 units (100%)

Experiment 4

Demonstrating the ability of heparin (irrespective of its form) to inhibit interferences present in clinical samples.

0.001 mg/ml protamine was used to simulate clinical sample interferences. Soluble heparin and insoluble heparin beads were used.

a) 25 µl protamine+25 µl antigen+950 µl extraction buffer (no heparin)=3.23 units (24.6%)
b) 25 µl protamine+25 µl antigen+100 µl heparin beads+ 835 µl extraction buffer (no heparin)=11.12 units (84.7%)
c) 25 µl protamine+25 µl antigen+950 µl extraction buffer with heparin=12.63 units (96.2%)
d) 25 µl antigen+950 µl extraction buffer (no heparin)= 13.13 units (100%)

What is claimed is:

1. In a method comprising detecting the possible presence of Chlamydia microorganisms in a clinical sample taken from a patient suspected of having a Chlamydia infection, wherein said clinical sample or an extract thereof is contacted with an aqueous extraction buffer effective to release lipopolysaccharide antigen from Chlamydia microorganisms if present and the resulting buffered extract is assayed for the presence of said Chlamydia lipopolysaccharide antigen, by means of an immunoassay using an antibody reagent specific for said Chlamydia lipopolysaccharide antigen, the improvement wherein said assay is carried out in the presence of an anionic polysaccharide in an amount sufficient to reduce assay interference caused by cations, said aqueous extraction buffer containing from about 0.1 mg/ml to about 10 mg/ml heparin and a surface active agent selected from the group consisting of 3-(3-chlolamidopropyl) dimethylammonio-1-propanesulfonate, 3-(3-chlolamidopropyl) dimethylammonio-2-hydroxyl-1-propanesulfonate and mixtures thereof, in an amount sufficient to release lipopolysaccharide antigen from cells of *Chlamydia trachomatis*.

2. A method of assaying for the possible presence of Chlamydia micro-organisms in a clinical sample taken from a patient suspected of having a Chlamydia infection comprising:

(a) extracting lipopolysaccharide antigen from Chlamydia microorganisms, if present in said clinical sample or an extract thereof, with a surface active agent;
(b) reducing assay interference caused by cations with an anionic polysaccharide; and
(c) detecting the presence of said Chlamydia lipopolysaccharide antigen by means of an immunoassay using an antibody reagent specific for said Chlamydia lipopolysaccharide antigen, from about 0.1% by weight to about 2% by weight of surface active agent being used to extract lipopolysaccharide antigen from Chlamydia micro-organisms.

3. A method of assaying for the possible presence of Chlamydia micro-organisms in a clinical sample taken from a patient suspected of having a Chlamydia infection comprising:

(a) extracting lipopolysaccharide antigen from Chlamydia microorganisms, if present in said clinical sample or an extract thereof, with a surface active agent;
(b) reducing assay interference caused by cations with an anionic polysaccharide; and
(c) detecting the presence of said Chlamydia lipopolysaccharide antigen by means of an immunoassay using an antibody reagent specific for said Chlamydia lipopolysaccharide antigen, from about a 0.1 mg/ml to about 10 mg/ml heparin being used to reduce assay interference caused by cations.

4. A method of assaying for the possible presence of Chlamydia micro-organisms in a clinical sample taken from a patient suspected of having a Chlamydia infection comprising:

(a) extracting lipopolysaccharide antigen from Chlamydia microorganisms, if present in said clinical sample or an extract thereof, with a surface active agent;
(b) reducing assay interference caused by cations with an anionic polysaccharide; and
(c) detecting the presence of said Chlamydia lipopolysaccharide antigen by means of an immunoassay using an antibody reagent specific for said Chlamydia lipopolysaccharide antigen, wherein the lipopolysaccharide antigen from Chlamydia micro-organisms, if present in said clinical sample or an extract thereof, is extracted and assay interference caused by cations is reduced with (i) from about 0.1% by weight to about 2% by weight of surface active agent and (ii) about 0.1 mg/ml to about 10 mg/ml heparin.

5. A method of assaying for the possible presence of Chiamydia micro-organisms in a clinical sample taken from a patient suspected of having a Chlamydia infection comprising:

(a) extracting lipopolysaccharide antigen from Chlamydia microorganisms, if present in said clinical sample or an extract thereof, with a surface active agent;
(b) reducing assay interference caused by cations with an anionic polysaccharide in insoluble form; and (c) detecting the presence of said Chlamydia lipopolysaccharide antigen by means of an immunoassay using an antibody reagent specific for said Chlamydia lipopolysaccharide antigen, from about 0.1% by weight to about 2% by weight of surface active agent being used to extract lipopolysaccharide antigen from Chlamydia micro-organisms.

6. A method according to claim 5, wherein said anionic polysaccharide is a glycosaminoglycan.

7. A method according to claim 5, wherein said anionic polysaccharide is heparin.

* * * * *